US010459257B2

(12) United States Patent
Rupasinghe et al.

(10) Patent No.: US 10,459,257 B2
(45) Date of Patent: Oct. 29, 2019

(54) CARBON-BASED SURFACE PLASMON SOURCE AND APPLICATIONS THEREOF

(71) Applicant: Monash University, Clayton (AU)

(72) Inventors: Chanaka Rupasinghe, Clayton (AU); Malin Premaratne, Camberwell (AU); Ivan D. Rukhlenko, Oakleigh (AU)

(73) Assignee: Monash University, Clayton, Victoria (AU)

( * ) Notice: Subject to any disclaimer, the term of this patent is extended or adjusted under 35 U.S.C. 154(b) by 679 days.

(21) Appl. No.: 15/048,520

(22) Filed: Feb. 19, 2016

(65) Prior Publication Data
US 2018/0252947 A1    Sep. 6, 2018

(30) Foreign Application Priority Data

Feb. 20, 2015 (AU) ................ 2015200886

(51) Int. Cl.
| | |
|---|---|
| *A61K 41/00* | (2006.01) |
| *G02F 1/00* | (2006.01) |
| *A61N 1/10* | (2006.01) |
| *A61N 5/06* | (2006.01) |
| *B82Y 20/00* | (2011.01) |

(52) U.S. Cl.
CPC .............. *G02F 1/0081* (2013.01); *A61N 1/10* (2013.01); *A61N 5/06* (2013.01); *A61N 5/062* (2013.01); *A61K 41/00* (2013.01); *A61K 41/0023* (2013.01); *A61K 41/0057* (2013.01); *B82Y 20/00* (2013.01)

(58) Field of Classification Search
CPC .......... A61N 1/10; A61N 5/06; G02F 1/0081; B82Y 5/00; B82Y 20/00
See application file for complete search history.

(56) References Cited

U.S. PATENT DOCUMENTS

| | | | |
|---|---|---|---|
| 7,569,188 B2 * | 8/2009 | Stockman | .............. B82Y 10/00 |
| | | | 422/82.05 |
| 8,017,406 B2 | 9/2011 | Stockman et al. | |

(Continued)

OTHER PUBLICATIONS

Duy Tho Pham, et al. Carbon Nanotube-Bridged Graphene 3D Building Blocks for Ultrafast Compact Supercapacitors, ACSNanom vol. 9 No. 2.2015.*

(Continued)

*Primary Examiner* — Carl H Layno
*Assistant Examiner* — Michael J Lau
(74) *Attorney, Agent, or Firm* — BakerHostetler (57) ABSTRACT

A spaser device comprises a graphene resonator and a carbon nanotube (CNT) gain element coupled via exciton-plasmon interaction. The graphene resonator may be a rectangular or square graphene nanoflake (GNF), and the CNT gain element may be characterized by chirality vector (n,m) selected such that the CNT has semiconducting properties. The CNT gain element may be illuminated using a light source having a photon energy corresponding with a first exciton energy ($E_{22}$) of the CNT, whereby excitons having a second exciton energy ($E_{11}$) less than the first exciton energy are generated in the CNT, and coupled to a surface plasmon (SP) mode of the graphene resonator. When the rate of generation of excitons having the second exciton energy exceeds a gain threshold, continuous spasing is established within the spaser device.

21 Claims, 8 Drawing Sheets

(56) References Cited

U.S. PATENT DOCUMENTS

| | | | | |
|---|---|---|---|---|
| 8,765,488 B2 * | 7/2014 | Strano | B82Y 15/00 435/14 |
| 8,894,886 B1 * | 11/2014 | Luhrs | C01B 32/192 252/378 R |
| 8,940,548 B2 * | 1/2015 | Khater | B82Y 10/00 436/524 |
| 8,951,561 B2 * | 2/2015 | Vo-Dinh | A61K 39/00 424/489 |
| 2004/0126304 A1 * | 7/2004 | Zhao | B82Y 10/00 423/447.2 |
| 2005/0069669 A1 * | 3/2005 | Sakaibara | B82Y 10/00 428/64.4 |
| 2009/0275065 A1 * | 11/2009 | Xing | C07D 501/04 435/18 |
| 2010/0003316 A1 * | 1/2010 | Vo Dinh | A61K 39/00 514/1.1 |
| 2010/0203391 A1 * | 8/2010 | Lopatin | B82Y 30/00 429/231.8 |
| 2010/0331758 A1 * | 12/2010 | Davalos | A61N 1/327 604/20 |
| 2011/0117202 A1 * | 5/2011 | Bourke, Jr. | H05B 41/2806 424/490 |
| 2012/0209344 A1 * | 8/2012 | Rossi | A61N 1/00 607/22 |
| 2012/0265122 A1 * | 10/2012 | El-Shall | A61K 41/0052 604/20 |
| 2012/0285660 A1 * | 11/2012 | Poltorak | F28F 21/02 165/104.11 |
| 2013/0062104 A1 * | 3/2013 | Craighead | B81B 3/0094 174/255 |
| 2014/0056551 A1 * | 2/2014 | Liu | G02F 1/025 385/2 |
| 2014/0073093 A1 * | 3/2014 | Farmer | B82Y 10/00 438/158 |
| 2014/0222117 A1 * | 8/2014 | Bourke, Jr. | A23L 3/26 607/88 |
| 2014/0225039 A1 * | 8/2014 | Chiang | B05D 1/02 252/478 |
| 2014/0234856 A1 * | 8/2014 | Reuel | G01N 33/5436 435/7.1 |
| 2014/0308194 A1 * | 10/2014 | Chan | B82Y 40/00 423/447.1 |
| 2014/0313636 A1 * | 10/2014 | Tour | H01G 11/72 361/502 |
| 2014/0342949 A1 * | 11/2014 | Wang | G01N 27/227 506/32 |
| 2014/0369954 A1 * | 12/2014 | Joshi | A61L 27/227 424/78.37 |
| 2015/0001993 A1 * | 1/2015 | Park | H01L 41/113 310/319 |
| 2015/0037240 A1 * | 2/2015 | Chen | B01J 37/18 423/447.3 |
| 2015/0044560 A1 * | 2/2015 | Ogino | H01M 4/134 429/217 |

OTHER PUBLICATIONS

Chang et al., "Theory for Bowtie Plasmonic Nanolasers", Optics Express, Jul. 2008, 16, 10580-10595.

Flynn et al., "A Room Temperature Semiconductor Spaser Operating Near 1.5 μm", Optics Express, Apr. 2011, 19, 8954-8961.

Li et al., "Electric Spaser in the Extreme Quantum Limit", Physical Review Letters, Mar. 2013, 110, 106803-1-106803-5.

Lisyansky et al., "Channel Spaser: Coherent Excitation of One-Dimensional Plasmons from Quantum Dots Located Along a Linear Channel", Physical Review B: Covering Condensed Matter and Materials Physics, Oct. 2011, 84, 153409-1-153409-4.

Noginov et al., "Demonstration of a Spaser-Based Nanolaser", Nature, Aug. 2009, 460, 1110-1112.

Vialla et al., "Chirality Dependence of the Absorption Cross Section of Carbon Nanotubes", Physical Review Letters, Sep. 2013, 111, 137402-1-137402-5.

Zheludev et al., "Lasing Spaser", Nature Photonics, Jun. 2008, 2, 351-354.

* cited by examiner

CARBON-BASED SURFACE PLASMON SOURCE AND APPLICATIONS THEREOF

FIELD OF THE INVENTION

The present invention relates to spaser (surface plasmon amplification by stimulated emission of radiation) devices, and in particular to structure, design and applications of carbon-based spaser devices.

BACKGROUND TO THE INVENTION

Nanoplasmonics offers tremendous new opportunities for fabricating ultrafast nanocircuits, as it permits miniaturization beyond the diffraction limit imposed on electromagnetic waves.

It is possible to use surface plasmons (SPs), the collective oscillations of electrons at metal-dielectric interfaces, to carry information at nanoscale. To power the circuits employing SPs, one needs an active device akin to a transistor in electronics or a laser in optics.

U.S. Pat. Nos. 7,569,188 and 8,017,406, to Bergman and Stockman, describe the principles of surface plasmon amplification by stimulated emission of radiation, and propose the use of this phenomenon to generate SPs in the active plasmonic device known as a spaser. A spaser broadly comprises a gain medium whose excitation energy is transferred nonradiatively to a coupled plasmonic resonator, increasing the amplitude of its localized SP modes. Spasers can generate much stronger coherent plasmonic fields than those created at a metallic surface excited by a laser source, due to the amplification of SPs through stimulated emission.

Experimental demonstration of the stimulated emission of SPs has resulted in the first practical realization, described in Noginov, M A et al., 'Demonstration of a Spaser-Based Nanolaser', *Nature* 2009, 460, 1110-1112, of a spaser comprising a spherical gold nanoparticle surrounded by dye-doped silica.

The operational characteristics of a spaser, such as plasmon generation rate, emission wavelength, SP quality factor, and threshold gain, strongly depend on the spaser's geometry and composition. Therefore, many spaser designs have been proposed and analyzed in search of the best performance. These include:

a gold-film plasmonic waveguide sandwiched between the optically pumped multiple quantum wells (QWs) (Flynn, R A et al., 'Room-Temperature Semiconductor Spaser Operating Near 1.5 μm', *Opt. Express* 2011, 19, 8954-8961);

a V-shaped metal nanoparticle surrounded by quantum dots (QDs) (U.S. Pat. Nos. 7,569,188 and 8,017,406);

an array of split-ring resonators on an active substrate (Zheludev, N et al., 'Lasing Spaser', *Nat. Photonics* 2008, 2, 351-354);

a bowtie-shaped metallic structure with bound QDs (Chang, S W et al., 'Theory For Bowtie Plasmonic Nanolasers', *Opt. Express* 2008, 16, 10580-10595.; and a metal nanogroove with QDs at its bottom (Lisyansky, A et al., 'Channel Spaser: Coherent Excitation of One-Dimensional Plasmons from Quantum Dots Located Along a Linear Channel', *Phys. Rev. B: Condens. Matter Mater. Phys.*, 2011, 84, 153409.

All of these prior art designs are based on the noble-metal plasmonic nanocavities of different geometries that were coupled to semiconductor QD/QW gain media.

In this emerging area of research and development there remains a need and opportunity for new spaser designs having advantageous characteristics, including one or more of: good performance; ability to vary designs to adapt or tune spasing parameters; ease of fabrication using known methods and materials; good mechanical properties; thermal stability; chemical stability; low toxicity; and biocompatibility. The present invention addresses this ongoing need.

SUMMARY OF THE INVENTION

In one aspect, the invention provides a spaser device comprising a graphene resonator and a carbon nanotube (CNT) gain element coupled via exciton-plasmon interaction.

Advantageously, embodiments of the invention are thus carbon-based, and offer many of the benefits associated with carbon materials, such as mechanical strength and flexibility, thermal and chemical stability, and suitability for use in biomedical applications.

Graphene and CNTs are the two allotropes of carbon that are widely used in optoelectronic applications due to their remarkable optical and electronic properties. They possess a honeycomb lattice structure, with carbon atoms being in $sp^2$ hybridization.

Graphene has more advantageous plasmonic properties than noble metals in terms of ease in tunability, field confinement, and resistive losses. For example, carriers in graphene behave as massless Dirac fermions because of their well-known conical bandstructure. The high concentration and mobility of the carriers allow graphene plasmons to travel much longer distances as compared to plasmons of noble metals.

Furthermore, semiconducting CNTs are well-known for supporting excitons, which can be created via optical absorption, and for having absorption and emission parameters that are strongly dependent on the CNT chirality. A CNT is therefore an advantageous gain medium for use in a spaser.

The graphene resonator may comprise a graphene nanoflake (GNF). The GNF may be rectangular, such that fabrication is simplified. In embodiments of the invention the GNF is square. The thickness of the square GNF may be, for example, less than or greater than 50 atoms. The properties of a GNF having thickness less than 50 atoms may be influenced by carrier confinement. The properties of a GNF having thickness greater than 50 atoms may advantageously be analysed using methods that do not account for carrier confinement.

The side length of the square GNF may be, for example, within the range of 25 nm to 100 nm, whereby the GNF resonator supports surface plasmon (SP) modes having energies falling at least within the range of 0.1 eV to 1.0 eV. The GNF may be adapted to tune an SP mode energy thereof to a selected value. For example, the GNF may be doped or gated in order to modify an associated Fermi energy ($E_F$) whereby a change in SP mode energy occurs. Advantageously, modification of $E_F$ may also be employed to reduce threshold gain of the spaser device and/or to enhance resonance of the SP mode.

The CNT gain element may comprise a single-walled CNT (SWNT) characterised by chirality vector (n,m) selected such that the SWNT has semiconducting properties. More particularly, the chirality of the SWNT may be selected such that a band-gap energy corresponds with an SP mode energy of the graphene resonator, e.g. within the range of 0.1 eV to 1.0 eV. Chirality vectors defining SWNTs having a band gap energy below 1.0 eV include: (13,11); (12,10); (16,2); (10,9); (12,4); (14,1); (11,3); (12,1); and (11,4).

Advantageously, the CNT gain element is configured for higher, rather than lower, emission and absorption cross sections. For example, the emission and absorption cross sections may each exceed $4 \times 10^{-6}$ cm$^2$. Chirality vectors defining SWNTs having a band gap energy below 1.0 eV and emission and absorption cross sections exceeding $4 \times 10^{-6}$ cm$^2$ include: (16,2); (12,4); (11,3); and (12,1).

The length of the CNT gain element may be selected in order to maximise coupling via the exciton-plasmon interaction. Advantageously, a ratio of GNF side length to CNT length may be within the range of 0.5 to 1.5, preferably within the range 1.0 to 1.3, and more preferably around 1.1. Furthermore, an orientation of the longitudinal axis of the CNT gain element relative to the graphene resonator may be selected in order to enhance coupling between CNT excitons and resonator SPs.

A spacing between the graphene resonator and the CNT gain element may also be selected so as to enhance coupling between CNT excitons and resonator SPs. In embodiments of the invention the spacing may be below 10 nm, and is more preferably around or below 5 nm. The spaser device may further comprise a layer of low refractive index dielectric material disposed as a spacing layer between the graphene resonator and the CNT gain element. The spacing layer may comprise, for example, SiO$_2$ or polydimethylsiloxane (PDMS).

In another aspect, the invention provides a method comprising:

providing a graphene resonator element and a carbon nanotube (CNT) gain element configured to form a spaser device according to the first-described aspect of the invention; and illuminating the CNT gain element using a light source having a photon energy corresponding with a first exciton energy of the CNT, whereby excitons having a second exciton energy less than the first exciton energy are generated in the CNT, and coupled to a surface plasmon (SP) mode of the graphene resonator, and wherein the rate of generation of excitons having the second exciton energy exceeds a gain threshold of the spaser device such that continuous spasing is established therein.

In another aspect, the invention provides a method of using a spaser device according to the first-described aspect for treatment of a medical condition, such as cancer, characterised by a growth of abnormal cells, the method comprising:

targeting the growth of abnormal cells with at least one graphene resonator element and at least one carbon nanotube (CNT) gain element to form a spaser device proximate to the growth; and illuminating the CNT gain element using a light source having a photon energy corresponding with a first exciton energy of the CNT, whereby excitons having a second exciton energy less than the first exciton energy are generated in the CNT, and coupled to a surface plasmon (SP) mode of the graphene resonator, and wherein the rate of generation of excitons having the second exciton energy exceeds a gain threshold of the spaser device such that continuous spasing is established therein, whereby an electric filed is generated proximate to the growth of abnormal cells sufficient to destroy the abnormal cells.

In embodiments of the invention, the step of targeting the growth of abnormal cells comprises functionalizing the graphene resonator element and the CNT gain element with one or more targeting agents to guide them towards the growth of abnormal cells. The targeting agents may be, for example, antibodies or receptor ligands.

Advantageously, the CNT gain element is adapted such that the first exciton energy corresponds with a photon energy within a mid- or near-infrared range for which tissues of a body undergoing treatment are substantially transparent.

The forgoing summary of the invention has been provided to illustrate certain key features, advantages and applications of the invention. Embodiments of the invention will now be described in greater detail, however it will be appreciated that these embodiments are presented by way of example, and are not intended to limit the scope of the invention as described in any of the preceding statements, or in the appended claims.

BRIEF DESCRIPTION OF THE DRAWINGS

Embodiments of the invention are described with reference to the accompanying drawings in which like reference numerals indicate like features, and wherein.

DETAILED DESCRIPTION OF EMBODIMENTS

Figure 1:
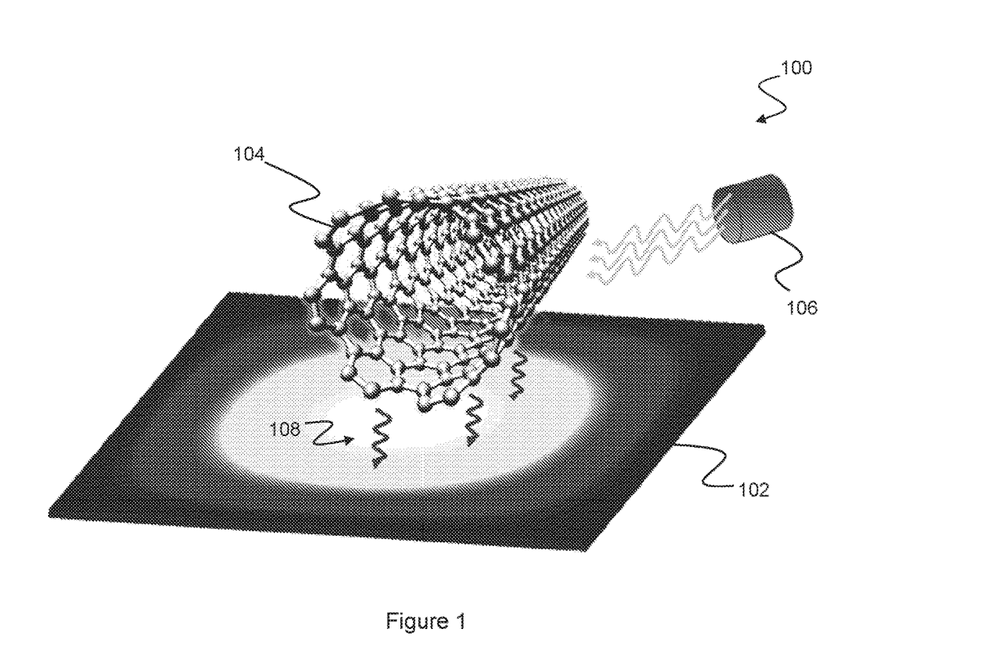
FIG. 1 is a schematic diagram illustrating a spaser device embodying the invention.

FIG. 1 is a schematic diagram illustrating a spaser device 100 embodying the invention. The device 100 employs a square graphene nanoflake (GNF) 102, having sides of length/width W, as a plasmonic resonator. This exemplary choice of the GNF's shape is made considering the simplicity of fabrication, and should not be regarded as limiting the scope of the invention. Although any rectangular graphene patch is easy to fabricate, a square shape reduces the number of geometric parameters without loss of generality.

The device 100 further comprises a carbon nanotube (CNT) 104. Semiconducting CNTs are known to supporting excitons, which can be created via optical absorption, and having absorption and emission parameters that are strongly dependent on the CNT chirality. As a result of these features, the present inventors have identified that CNTs may advantageously be employed as a gain medium for a spaser device 100.

For a given width W of the GNF 102, the resonator supports a series of localized SP modes of unique energies. The device 100 may be configured such that these modes spatially and spectrally overlap with the CNT excitons in different degrees and therefore experience different amounts of gain. An SP mode that is in resonance with the emission line of the CNT survives, receiving the maximum gain. This dominant mode is known as the 'spaser mode'.

In order to maintain continuous spasing, we assume that the CNT 104 is excited by a suitable pump source. Because of the large absorption coefficient of CNTs at optical frequencies, we consider optical pumping, represented in the device 100 by laser source 106. However, other forms of pumping are possible. For example, electrical pumping of such a CNT gain element has been demonstrated using a quantum wire based spaser design (Li, D., Stockman, M. I. 'Electric Spaser in the Extreme Quantum Limit', *Phys. Rev. Lett.* 2013, 110, 106803). The excitons of the CNT generated by the pump recombine and nonradiatively transfer their energy 108 to the GNF plasmons. The excited SPs stimulate the CNT to excite more SPs of the same mode and energy, resulting in a buildup of the spasing mode intensity.

Plasmonic properties of graphene are characterized by its frequency dependent optical conductivity, which is also a function of Fermi energy $E_F$. Since $E_F$ can be controlled by doping or electrostatic gating, the plasmonic properties of graphene are readily tunable.

Following the semiclassical Drude model with a finite temperature correction, the conductivity of graphene can be written as $$\sigma(\omega) = \frac{e^2 E_F}{\pi \hbar^2} \frac{2i k_B T}{\omega + i\tau^{-1}} \ln\left[2 \cosh\left(\frac{E_F}{2k_B T}\right)\right] \quad (1)$$

In Equation 1, e is the charge of the electron, $\omega$ is the SP frequency, $\tau$ is the relaxation time, $k_B$ is the Boltzmann's constant, and T is the temperature of the system. Although this expression is derived for an infinitely wide graphene sheet, it provides a reasonably accurate estimate for GNFs of lateral sizes exceeding 50 atoms. It becomes less accurate in much narrower graphene sheets because of the extreme carrier confinement. For this reason, we consider GNFs to be large enough to avoid the effects of carrier confinement. Since SPs are tightly confined by the GNF's surface, they can strongly interact with the nanotubes excitons, 18 which makes a GNF an excellent plasmon resonator for a spaser.

Figure 2A:
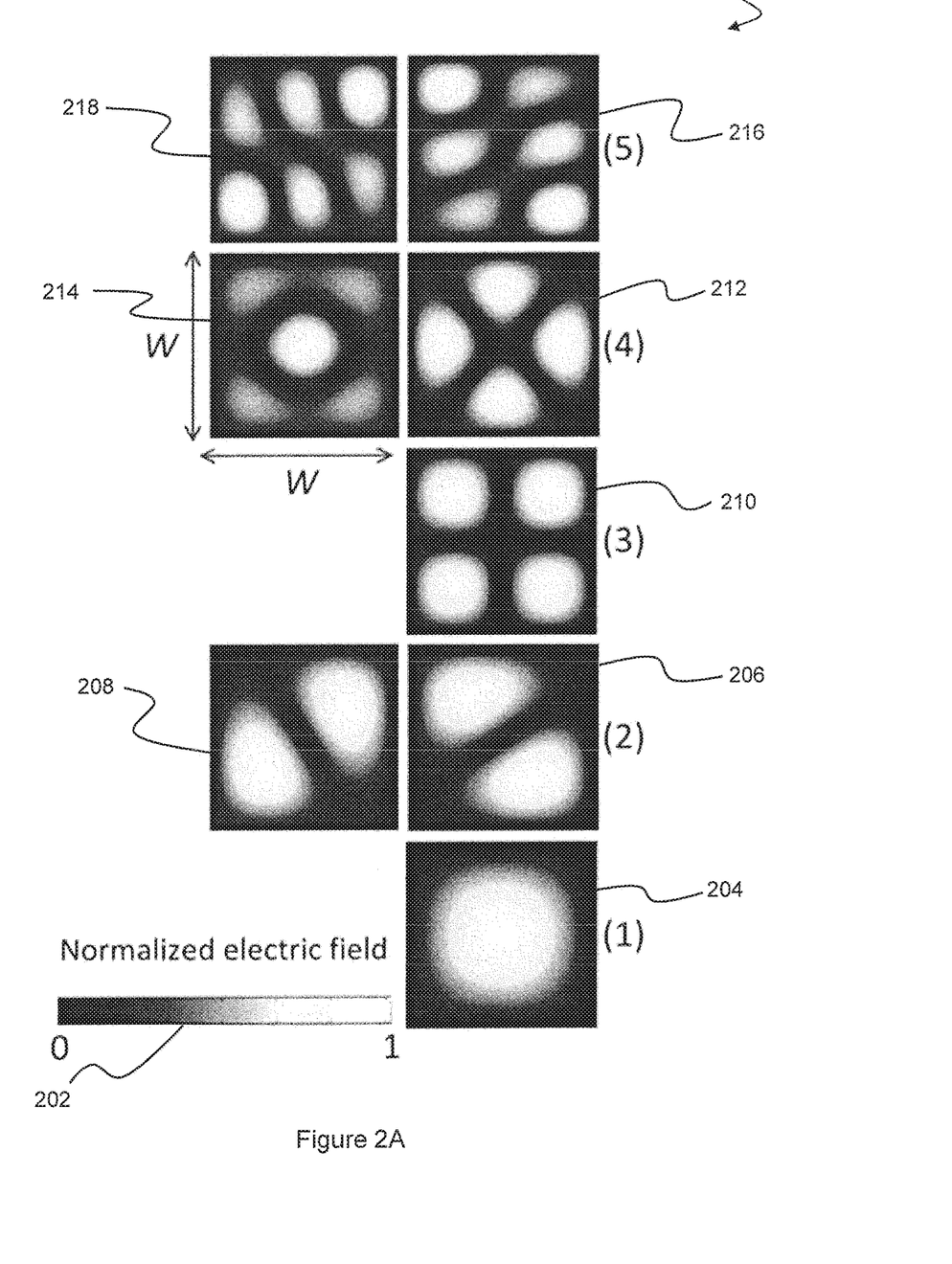
FIG. 2A shows computed electric field distributions of five low-energy modes of a graphene resonator embodying the invention.

A GNF supports a set of SP modes whose frequencies and field distributions can be found by solving the Helmholtz wave equation with appropriate boundary conditions (see Appendix A). FIG. 2A shows computed electric field distributions 200 of five low-energy modes of a graphene resonator embodying the invention, where they are numbered consecutively by index l=1, 2, 3, . . . , in order of increasing energy. Electric field strength is represented by shading according to the scale 202. Modes 1 and 3 each have a single field distribution 204, 210. Modes 2, 4, and 5 are seen to be doubly-degenerate, as illustrated by the pairs of distributions (206, 208), (212, 214) and (216, 218) respectively. Therefore, each SP mode may be characterized by a pair (l, η) of integers, which are the number and degeneracy of the mode.

Figure 2B:
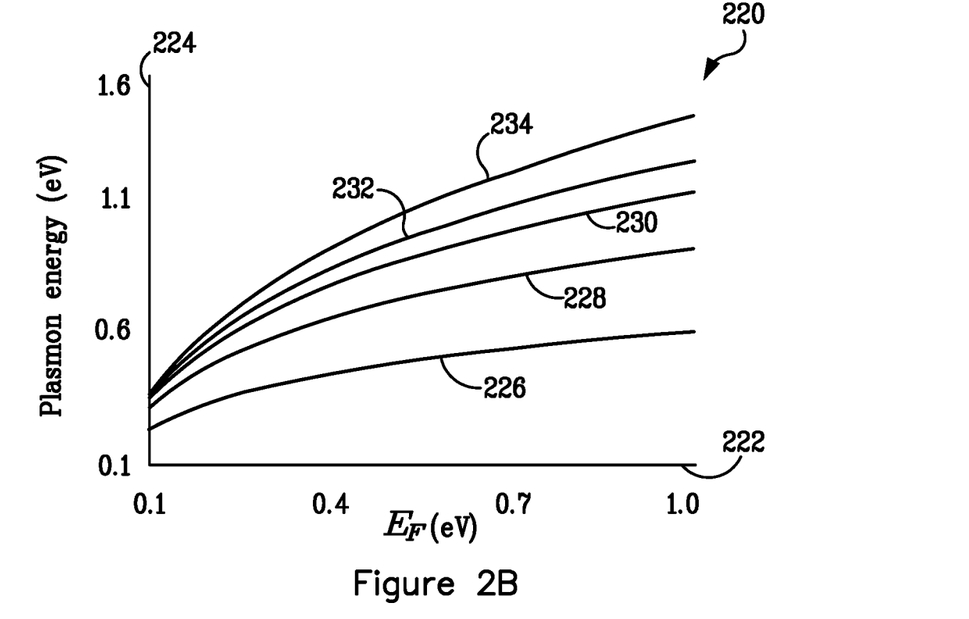
FIGS. 2B and 2C are graphs showing plasmon mode energies corresponding with graphene resonators embodying the invention, for the modes illustrated in FIG. 2A.
Figure 2C:
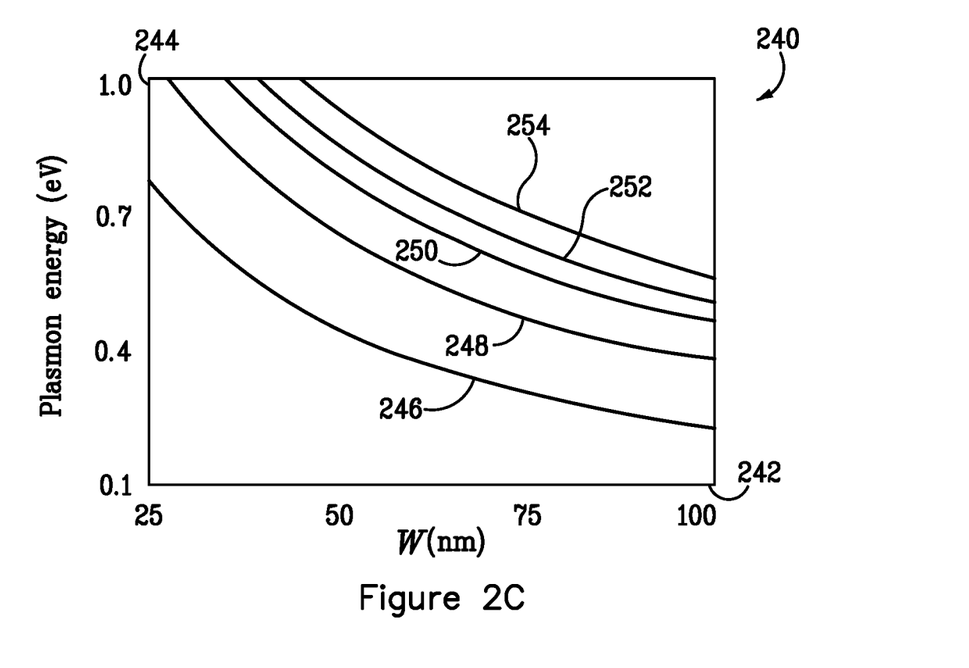

The tunability of the mode energies with the Fermi energy $E_F$ and the GNF width W are illustrated in FIGS. 2B and 2C, which comprise graphs 220, 240 showing plasmon mode energies corresponding with graphene resonators embodying the invention.

FIG. 2B is a graph 220, in which Fermi energy $E_F$ is shown on the horizontal axis 222, while plasmon energy is shown on the vertical axis 224. The energies of the five lowest energy modes having indices l=1, 2, 3, 4, 5 are shown by the curves 226, 228, 230, 232, 234 respectively. FIG. 2C is a graph 240, in which GNF width W is shown on the horizontal axis 242, while plasmon energy is shown on the vertical axis 244. The energies of the five lowest energy modes having indices l={1 . . . 5} are shown by the curves 246, 248, 250, 252, 254 respectively.

The energies are seen to vary over a wide range (from mid- to near-infrared frequencies) offering a great flexibility in spaser design. Moreover, the two dependencies are similar to those for one-dimensional graphene nanoribbons, which scale as $\sqrt{E_F}$ and $1/\sqrt{W_r}$. Since $E_F$ can be changed by either doping or gating, the mode energies are tunable via alterations of both the geometric and material parameters of the GNF.

The fields of the SP modes are quantized to study their interactions with the CNT using a convenient quantum mechanical framework.

The energy of the excited CNT is transferred nonradiatively to the GNF via the exciton plasmon interaction. As was mentioned earlier, the CNT is chosen as a gain element because of its high optical absorption and strong photoluminescence efficiency. Recent studies revealed that the transitions involved in these phenomena occur between the states of the CNT excitons, which arise because of the unique electronic properties of CNTs related to their molecular structure.

The CNT may be formed by rolling a graphene sheet around a certain chirality vector defined by a pair of integers (n,m). The electronic band structure and the density of states (DOS) of such a CNT can be calculated using the tight-binding model for π electrons of carbon atoms, followed by the zone-folding technique (see Appendix A).

Figure 3A:
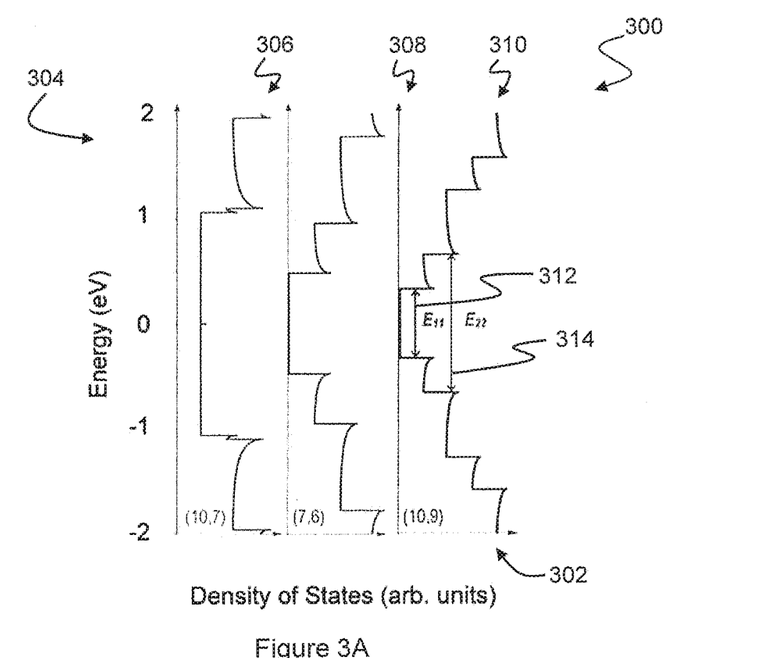
FIG. 3A shows computed density of states for exemplary carbon nanotube gain elements embodying the invention.

It is easy to show that the CNT can be either metallic or semiconducting depending on its chirality, i. e. on whether |(n-m) mod 3| is zero or not. FIG. 3A shows computed density of states 300 for exemplary carbon nanotube gain elements embodying the invention, where the horizontal axis 302 is DOS, and the vertical axis 304 represents energy. The DOS 306 of the (n,m)=(10,7) CNT is everywhere nonzero, indicating metallic behaviour of the nanotube. In contrast to this, the DOS 308 of the (7,6) CNT and the DOS 310 of the (10,9) CNT exhibit wide bandgaps, which implies that both nanotubes behave as semiconductors. The peaks in the DOS, known as Van Hove singularities, facilitate the formation of the well-defined exciton states of energies that enable optical transitions.

The energies of the states can be readily found using the DOS plots. The first two exciton energies $E_{11}$ and $E_{22}$ of the (10,9) CNT are indicated by reference numerals 312, 314.

A spaser may therefore be designed such that the pump laser resonantly excites a semiconducting CNT and generates excitons of energy $E_{22}$. The excitons then relax to the lower state of energy $E_{11}$, while the excess of energy $E_{22}$-$E_{11}$ is absorbed by an additional resonant system, which eventually transfers this energy to a bath. If the energy of a GNF SP mode coincides with $E_{11}$ and the GNF is located close to the CNT, then the excitons may annihilate and transfer their energy to plasmons.

Figure 3B:
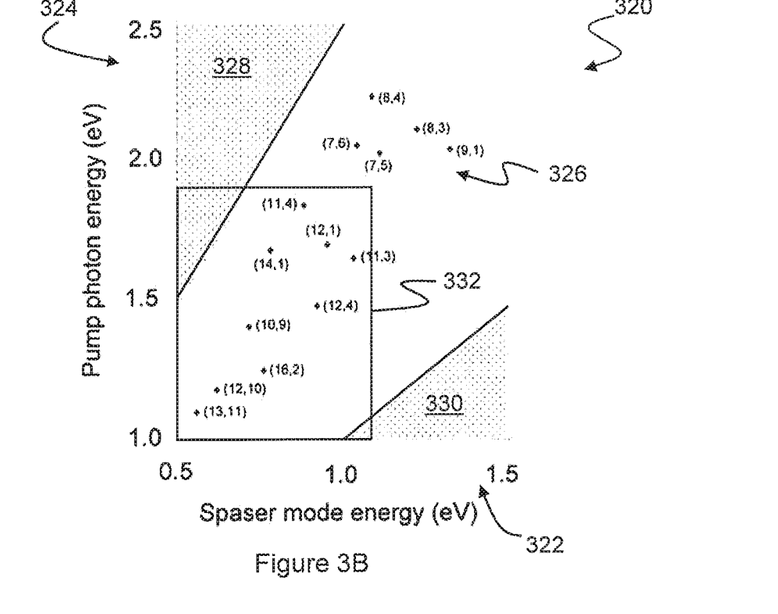
FIG. 3B is a graph representing a set of usable carbon nanotube gain elements embodying the invention.

FIG. 3B is a graph 320 representing a set of usable carbon nanotube gain elements embodying the invention. In the graph 320 the horizontal axis 322 is spaser mode energy, while the vertical axis 324 is pump photon energy. Points 326 within the graph represent nanotubes of different chiralities that can be used in different spaser configurations. There are no nanotubes in the regions 328, 330 because $E_{22}$ must be greater than $E_{11}$. The nanotubes within the area 332 are the most favourable for spaser operation, because the energies of most of the GNF modes are below 1 eV, as shown in FIGS. 2B and 2C, and the energy difference $E_{22}$-$E_{11}$ for such CNTs is relatively small. Hence, for preset ranges of the emission and pumping wavelengths of the spaser, its performance can be optimized by selecting one of the CNTs from the favourable region 332.

Figure 4:
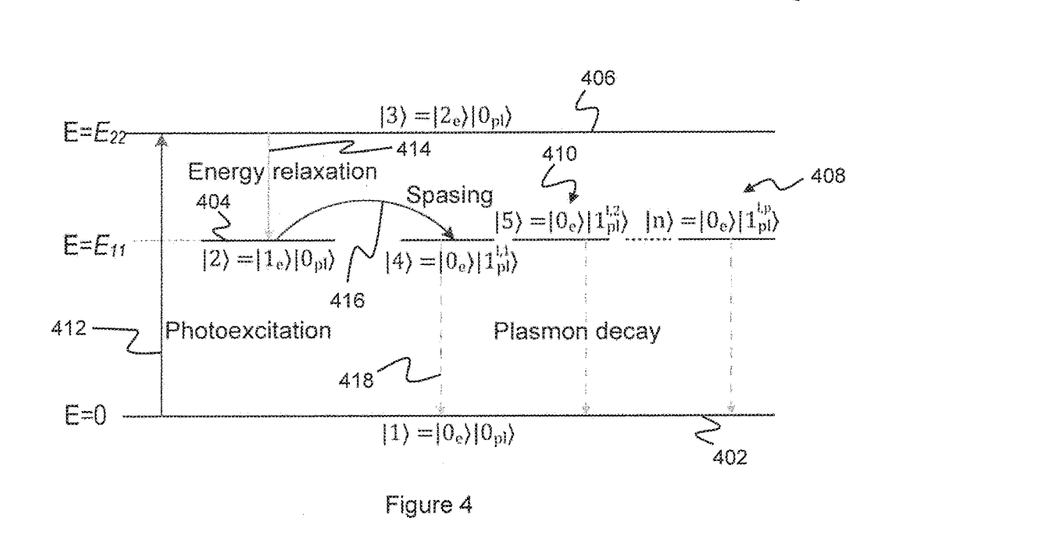
FIG. 4 is an energy level diagram illustrating a quantum mechanical model of a spaser device embodying the invention.

The spaser may be modelled as a quantum system whose states are the product of the states of the CNT excitonic subsystem and the GNF plasmonic subsystem. An energy level diagram 400 illustrating a quantum mechanical model of a spaser device embodying the invention is shown in FIG. 4. It is assumed that the excitons have three states, the ground state $|0_e\rangle$ 402 of zero energy and the two excited states $|1_e\rangle$ 404 and $|2_e\rangle$ 406 of energies $E_{11}$ and $E_{22}$, whereas the plasmon mode l of degeneracy p can be in one of p+1 states 408. The vacuum of plasmon modes is denoted as $|0_{pl}\rangle$, and the degenerate states (e.g. state 410) of the mode of energy $E_{SP}$ are denoted as $|1_{pl}^{l,1}\rangle$, $|1_{pl}^{l,2}\rangle$, ..., $|1_{pl}^{l,p}\rangle$.

In the presence of pump photons of energy $E_{22}$ photoexcitation 412 occurs from the exciton ground state 402 to the upper excited state 406. Relaxation 414 subsequently occurs to the lower excited state 404. Energy transfer can occur from excitons in the lower excited state 404 to one or more of the plasmon modes 408 via exciton-plasmon interaction, i.e. spasing, 416. Plasmon energy may be released by decay 418 to the ground state 402.

Using the above notation, the essential p+3 states of the spaser are as follows:

$|1\rangle = |0_e\rangle|0_{pl}\rangle$, $|2\rangle = |0_e\rangle|0_{pl}\rangle$, $|3\rangle = |2_e\rangle|0_{pl}\rangle$, $|4\rangle = |0_e\rangle|1_{pl}^{l,1}\rangle$, $|5\rangle = |0_e\rangle|1_{pl}^{l,2}\rangle$, ..., $|p+3\rangle = |0_e\rangle|1_{pl}^{l,p}\rangle$ This set of states enables the effects of the SP mode degeneracy on spaser characteristics to be studied. A (p+3)×(p+3) density matrix of the spaser may be constructed, the dynamics of which are described by the following master equation for the density operator $\hat{\rho}$:

$$\frac{\partial \rho_{\mu\nu}}{\partial t} = \frac{1}{i\hbar}[\hat{H}, \hat{\rho}]_{\mu\nu} - \gamma_{\mu\nu}\rho_{\mu\nu} + \delta_{\mu\nu}\sum_{K \neq \nu}\xi_{\nu K}\rho_{KK} \quad (2)$$

In Equation 2, $\hat{H}$ is the Hamiltonian of the spaser, $\gamma_{\mu\nu}$ is the coherence relaxation rate between the states $|\mu\rangle$ and $|\nu\rangle$, and $\xi_{VK}$ is the transition rate from state $|k\rangle$ to state $|v\rangle$. The first term on the right-hand side of this equation represents the time evolution of $\hat{\rho}$ and comes from the quantum Liouville equation, whereas the rest of the right-hand side part is the relaxation superoperator accounting for the dissipation of the density matrix components.

Equation 2 is a system of linear partial differential equations, the solution of which can lead to population inversion (i.e. $F_{22}$>$F_{11}$) for a sufficiently strong pump and sufficiently fast energy relaxation 414 between the excitonic states 406, 404.

The master equation is solved to calculate the plasmon generation rate by considering an arbitrary spaser mode l of degeneracy p. The plasmon generation rate of this mode is defined as a the total steady-state population of the mode, which is given by the sum $R_l = F_{44} + F_{55} + \ldots + F_{p+3,p+3}$. Since the degeneracy order of the first five SP modes does not exceed two (as discussed above with reference to FIG. 2A), a spaser operating in one of these modes has either four or five essential states.

By solving Equation 2 for the case of stationary excitation, the plasmon generation rate is given by (see Appendix A):

$$R_{l,p} = \alpha \omega_l^2 \frac{\gamma_p}{\gamma_p^2 + \Delta_p^2} |V_L|^2 \sum_{\eta=1}^{p} |V_{l,\eta}|^2 \quad (3)$$

In Equation 3, $\alpha$ is a constant, which depends on the environment and material parameters of the CNT, $\gamma_p = \gamma_{24} = \gamma_{25}$, $\Delta p = (E_{11} - E_{SP})/\hbar$, and $V_L = \langle 2_e | E_L \cdot r | 0_e \rangle$ and $V_{l,\eta} = \langle 1_e | E_{l,\eta} \cdot r | 0_e \rangle$ are the matrix element of exciton interaction with the excitation light field $E_L$ and the field $E_{l,\eta}$ of the GNF SP mode (l,η).

Figure 5A:
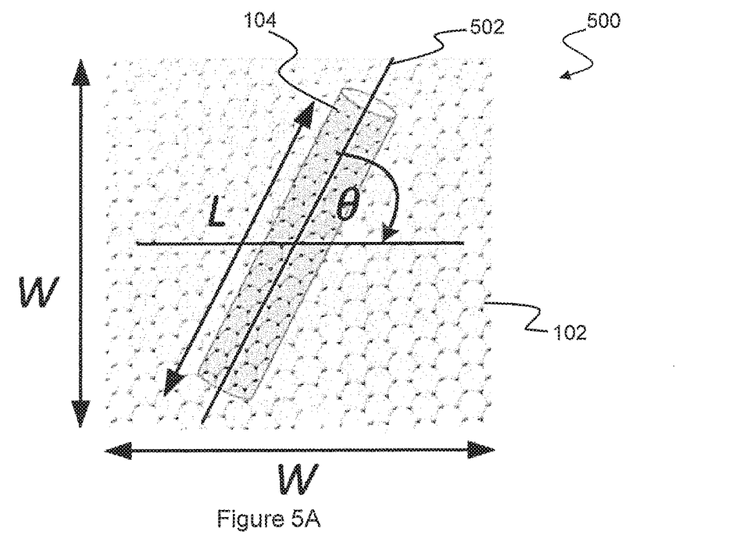
FIG. 5A is a schematic diagram illustrating relative positions and dimensions of a graphene resonator and a carbon nanotube gain element arranged as a spaser device embodying the invention.

Using this expression, the performance of the spaser as a function of its material and geometric parameters may be studied. FIG. 5A is a schematic diagram 500 illustrating relative positions and dimensions of a graphene resonator 102 of width W and a carbon nanotube gain element 104 of length L arranged as a spaser device embodying the invention. The CNT 104 is located at distance H parallel to the surface of the GNF 102. In the embodiment shown, the centres of the GNF 102 and CNT 104 coincide, while the nanotube's longitudinal axis 502 makes an angle θ with the GNF edge.

The following discussion relates to results for GNFs 102 having widths W between 25 and 100 nm, for which the conductivity model employed is accurate enough. The nanotube 104 length L is varied from 0.2 W to 2.5 W, and H is kept within the range of 5-20 nm, which allows for the near-field interaction 416 between the GNF SP modes and CNT excitons.

In order to study the plasmon generation rate of the proposed spaser 500, the exciton-plasmon matrix elements $V_{l,\eta}$ are numerically evaluated by assuming that the exciton state along the CNT 104 is described by the symmetric (with respect to the CNT's centre) Gaussian wave function. Inhomogeneity of the plasmonic field across the nanotube's diameter is neglected.

Figure 5B:
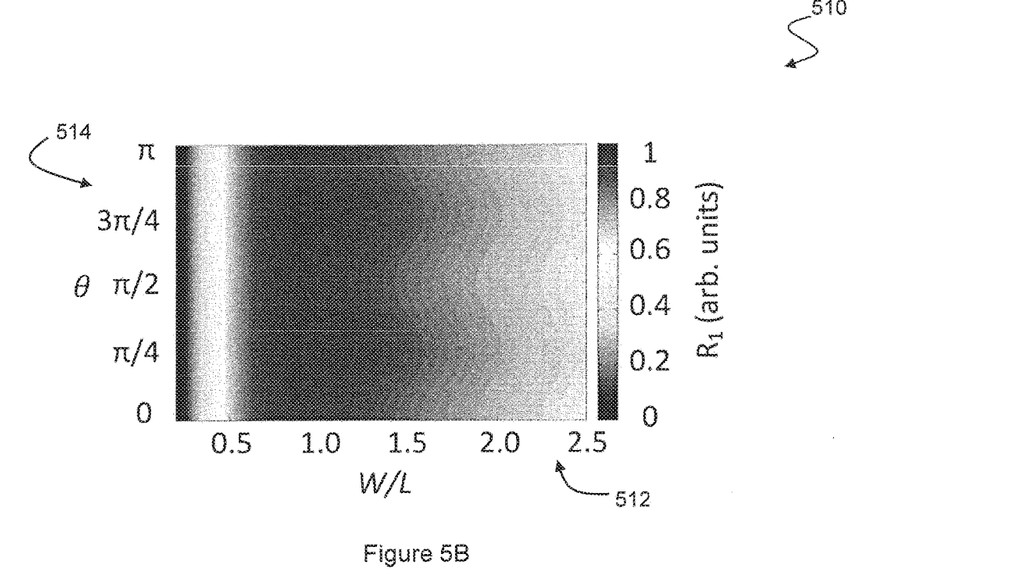
FIGS. 5B and 5C show computed plasmon generation rates for a range of arrangements represented by FIG. 5A.
Figure 5C:
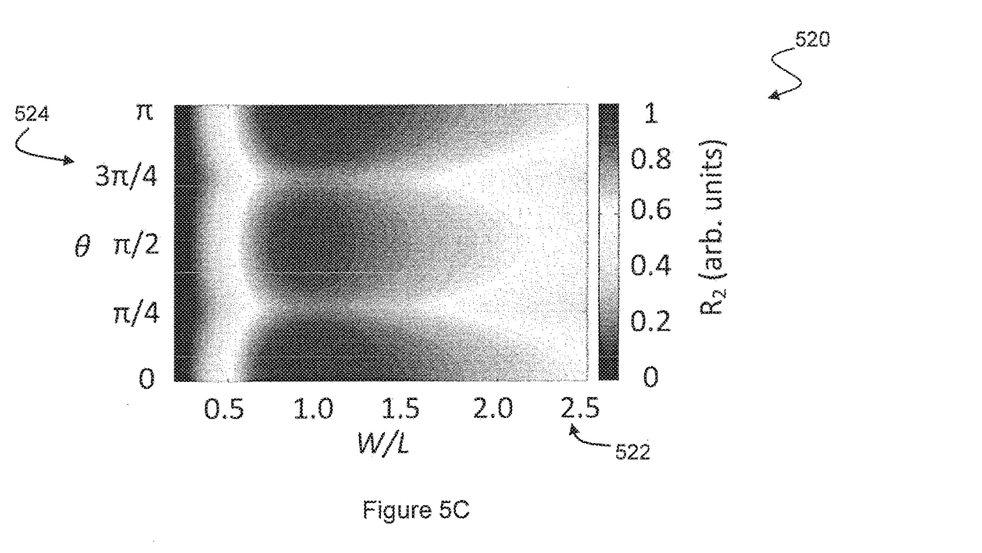

FIGS. 5B and 5C show computed plasmon generation rates for a range of arrangements 500 represented by FIG. 5A. FIG. 5B is a chart 510 of plasmon generation rate $R_1$ for the mode l=1 in which the horizontal axis 512 is the ratio of GNF width W to CNT length L, and the vertical axis 514 is the angle θ. FIG. 5C is a chart 520 of plasmon generation rate $R_2$ for the mode l=2 in which the horizontal axis 522 is the ratio of GNF width W to CNT length L, and the vertical axis 524 is the angle θ. In both cases H=5 nm. It can be seen that both $R_1$ and $R_2$ peak for L≈1.1 W, with their absolute maxima achieved for θ=π/4+(π/2)k and θ=πk (k=0, 1, 2, . . .), respectively. The optimal angles are determined by the distributions of the electric field of the SP modes (as shown in FIG. 2A), which is why the mutual orientation of the CNT 104 and GNF 102 is crucial for spaser performance and should be chosen depending on the spasing mode.

When the length of the CNT 104 is less than the optimal length, the plasmon generation rate reduces because of the reduction in the CNT's dipole moment. When the length of the CNT 104 exceeds the optimal length, the reduction in the plasmon generation rate is explained by the reduced spatial overlap between the SP mode field and the nanotube's excitons.

Figure 5D:
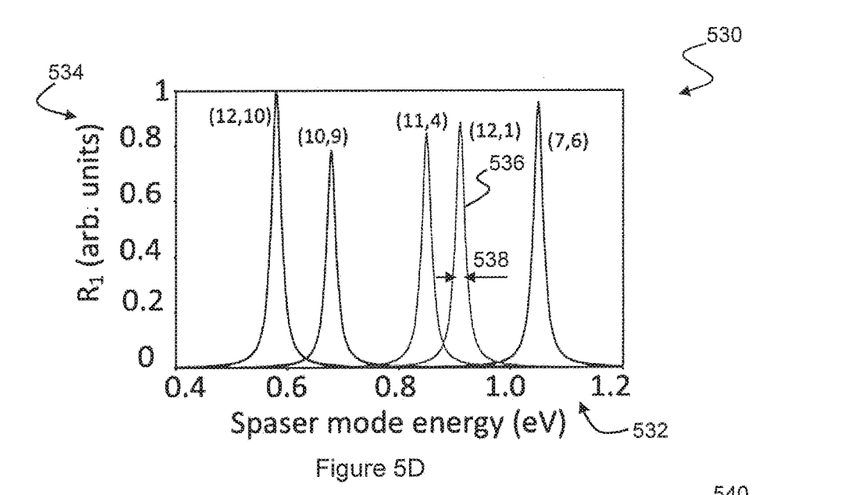
FIG. 5D is a graph showing plasmon generation rate as a function of mode energy corresponding with exemplary carbon nanotube gain elements embodying the invention.

To achieve the maximal spasing efficiency, the spaser mode should be resonantly coupled to the lower excitonic state. The coupling can be realized by matching the GNF's SP mode energy with the energy of the lower excitonic state via changing W or $E_F$ (as discussed above with reference to FIGS. 2B and 2C). FIG. 5D is a graph 530 showing how the rate $R_1$ (vertical axis 534) varies with the SP mode energy (horizontal axis 532) for five CNTs, θ=π/4, L=1.1 W, W=35 nm, and H=5 nm. By way of example, the CNT with (n,m)=(12,1) corresponds with peak 536 of width 538.

The widths of the spectra in the graph 530 can be combined with the results shown in the graph 240 of FIG. 2C to determine that the realization of resonant plasmon-exciton coupling would require a fabrication tolerance of about 1 nm, if matching is to be achieved by selection of the GNF width W. Resonance between GNF plasmons and CNT excitons may additionally, or alternatively, be achieved by doping the nanotube, oxidizing it, or having multiple carbon layers in its wall.

Figure 5E:
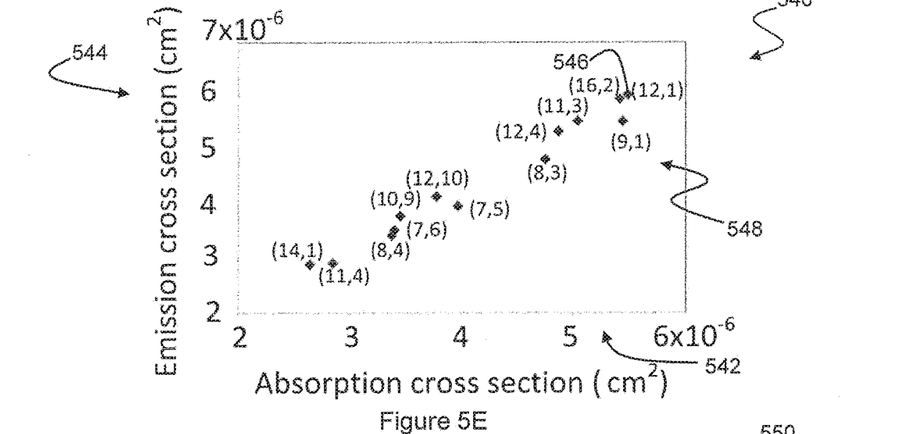
FIG. 5E is a graph showing emission and absorption cross sections at resonance corresponding with exemplary carbon nanotube gain elements embodying the invention.

If several CNTs have the desired exciton spectrum, then the preference should be given to the nanotube with the highest emission and absorption cross sections at resonance. FIG. 5E is a graph 540 showing absorption (horizontal axis 542) and emission (vertical axis 544) cross sections at resonance corresponding with exemplary carbon nanotube gain elements embodying the invention. The positions of the nanotubes on the figure were obtained using empirical formulas as described in Vialla, F et al, 'Chirality Dependence of the Absorption Cross Section of Carbon Nanotubes,' *Phys. Rev. Lett.* 2013, 111, 137402. For example, the (n,m)=(12,1) CNT corresponding with the peak 536 in FIG. 5D is represented by the point 546. The CNTs 548 located in the right top corner of FIG. 5E have the highest emission and absorption cross sections, and are thus most advantageous, all else being equal.

Figure 5F:
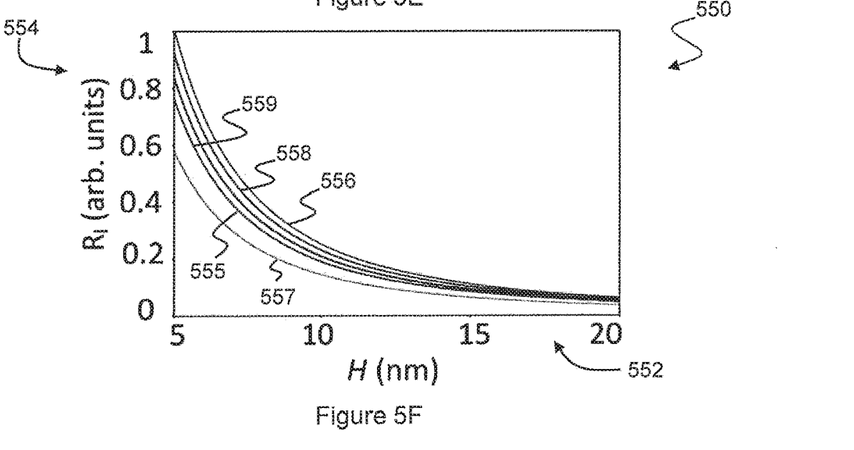
FIG. 5F is a graph showing plasmon generation rates for the modes illustrated in FIG. 2A, as a function of separation between a graphene resonator and a carbon nanotube gain element arranged as a spaser device embodying the invention.

FIG. 5F is a graph 550 showing plasmon generation rates $R_l$ (vertical axis 554) for the modes l={1 . . . 5} (curves 555, 556, 557, 558 and 559, respectively) illustrated in FIG. 2A, as a function of separation H (horizontal axis 552) between the GNF 102 and CNT 104. The graph 550 illustrates the impact of the near-field coupling between the CNT and GNF on the plasmon generation rate, and shows how $R_l$ varies with the distance from the nanotube 104 to the GNF's plane for the first five plasmon modes. The optimal spaser parameters are employed in all cases: L=1.1 W, W=35 nm, θ=π/4 for l={1,3}, and θ=0 for the rest of the modes. The plasmon generation rate is seen to monotonously decrease with the CNT moving away from the GNF for all spaser modes. The rates corresponding to the degenerate modes (with l=2, 4, and 5) are slightly larger than for the nondegenerate ones, because of the stronger spatial overlap of their near fields with the CNT excitons.

Figure 5G:
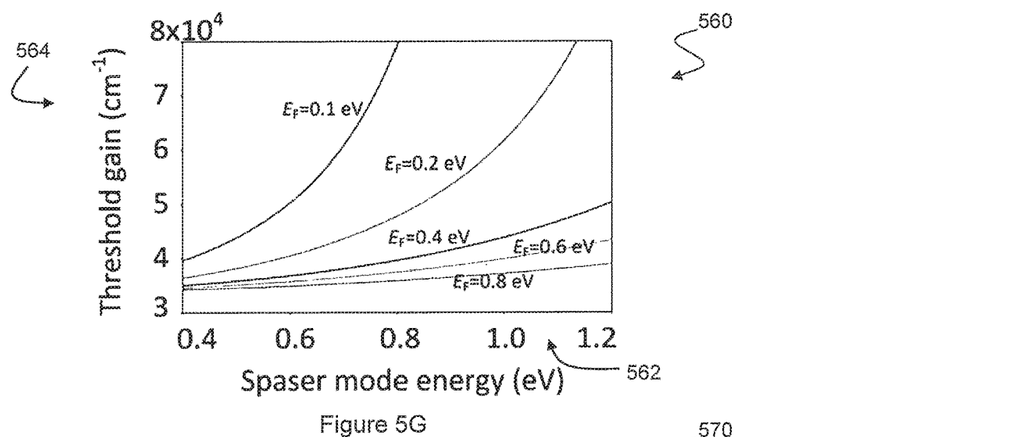
FIG. 5G is a graph illustrating threshold gain as a function of spaser mode energy for exemplary spaser devices embodying the invention.

In addition to the plasmon generation rate, it is important to analyze the threshold gain required for continuous spasing. This gain is known to predominantly depend on the dielectric properties of spaser materials. FIG. 5G is a graph 560 illustrating threshold gain (vertical axis 564) as a function of spaser mode energy (horizontal axis 562) for a set of exemplary spaser devices 500 in which the Fermi energy of the GNF 102 is $E_F$={0.1 eV, 0.2 eV, 0.4 eV, 0.6 eV, 0.8 eV}. The graph 560 shows that the threshold gain grows exponentially with the spaser mode energy. For a given value of $E_{SP}$, the spasing threshold can be significantly reduced by doping the GNF 102 and increasing its Fermi energy.

Figure 5H:
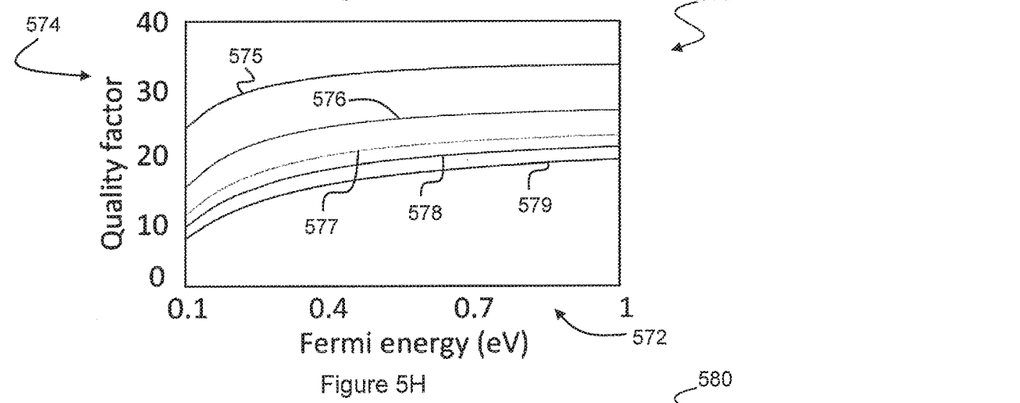
FIG. 5H is a graph illustrating quality factor of graphene resonators embodying the invention over a range of Fermi energy, for the modes illustrated in FIG. 2A.

FIG. 5H is a graph 570 illustrating quality factor (vertical axis 574) of graphene resonators embodying the invention over a range of Fermi energy (horizontal axis 572), for the modes l={1 . . . 5} (curves 575, 576, 577, 578 and 579, respectively) illustrated in FIG. 2A. The graphs 560, 570 show that doping simultaneously improves spasing threshold and the quality factor of the GNF resonator, which would in turn result in lower losses and improved spaser performance.

Figure 5I:
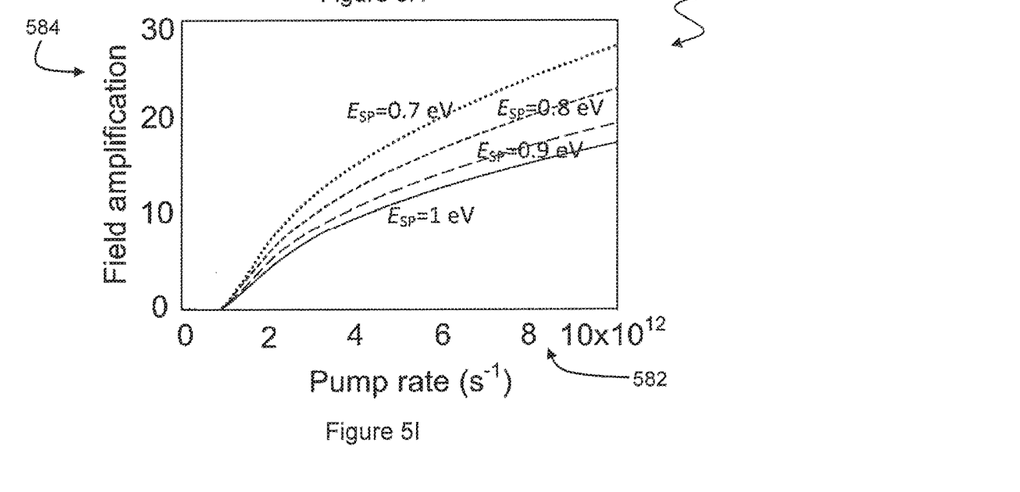
FIG. 5I is a graph illustrating field amplification as a function of pumping rate for exemplary spaser devices embodying the invention.

FIG. 5I is a graph 580 illustrating field amplification (vertical axis 584) as a function of pumping rate (horizontal axis 582) for exemplary spaser devices in which the spaser mode energy is $E_{SP}$={0.7 eV, 0.8 eV, 0.9 eV, 1.0 eV}. When the pump rate exceeds the corresponding threshold gain, plasmon population increases with the pump rate and field is amplified. The maximum practical pump rate may depend upon the application of the spaser, and in particular upon the maximum safe operating intensity of the pump laser 106. Notably, however, the greatest benefits of increasing pump rate are realised up to rates of around $2\text{-}4\times10^{12}$ s$^{-1}$, beyond which a decrease in slope efficiency is observed.

The analysis of the spaser performance demonstrates that the design is highly tunable and can be optimized to achieve the maximum SP generation rate. In particular, the spaser mode energy can be varied from 0.2 eV to 1.2 eV, spanning across a wide range of near- and mid-infrared frequencies. The emission energy can be tuned within this range by changing the geometric parameters (W, L, and θ) and the material parameters ($E_F$ and CNT chirality) of the spaser. The results presented in FIGS. 2, 3, and 5 provide the necessary information for such a parametric tuning.

For instance, to design a spaser emitting at the 1362 nm wavelength (which corresponds to the SP mode energy of 0.91 eV), the second mode of a sufficiently doped, 38 nm wide GNF with $E_F$=0.4 eV may be employed, in accordance with the data shown in FIG. 2C. According to FIGS. 3B and 5B, the most efficient excitation of this mode may be achieved using a 34 nm long CNT of chirality vector (12,1) oriented parallel to a pair of the GNF's edges (θ=0). The pumping wavelength is then set around 730 nm. This example shows that the results obtained may serve as design guidelines for the realization of a GNF/CNT-based spaser.

The many tuning parameters of the spaser significantly facilitate its fabrication by making the suggested design flexible.

The proposed spaser can be experimentally realized using common nanofabrication techniques. A graphene sheet can be formed using such methods as chemical vapor deposition (CVD), micromechanical cleavage, graphite oxide exfoliation, or epitaxial growth on a substrate. When the spaser's emission wavelength (or the spaser mode energy) is chosen, FIG. 2C enables one to select the appropriate width of the GNF to be patterned using a convenient method, e.g. lithography, transfer printing, or direct laser shaping. The GNF can then be transferred to a low-index dielectric substrate such as $SiO_2$ or polydimethylsiloxane (PDMS).

A suitable CNT, selected according to the pumping and emission energies shown in FIG. 3B, can be fabricated using CVD or other convenient technology. The distance between the GNF and CNT can be controlled by depositing a layer of the substrate material on the top of the GNF. This may introduce weak substrate effects, such as a small shift of the spasing wavelength, which can be neglected if the substrate material is of low refractive index and nondispersive.

In addition to broad tunability, the proposed spaser design offers such advantages as mechanical strength and thermal stability due to the unique properties of both graphene and CNTs. It can be used as an active element in plasmonic nanocircuits, which overcome the miniaturization and bandwidth limitations of the conventional optical and electronic circuits. The devices employing these circuits would inherit the favourable properties of carbon allotropes. The possible applications of spasers made of GNFs and CNTs range from ultrafast processors and flexible electronics to high-temperature devices and biomedical sensing.

Figure 6:
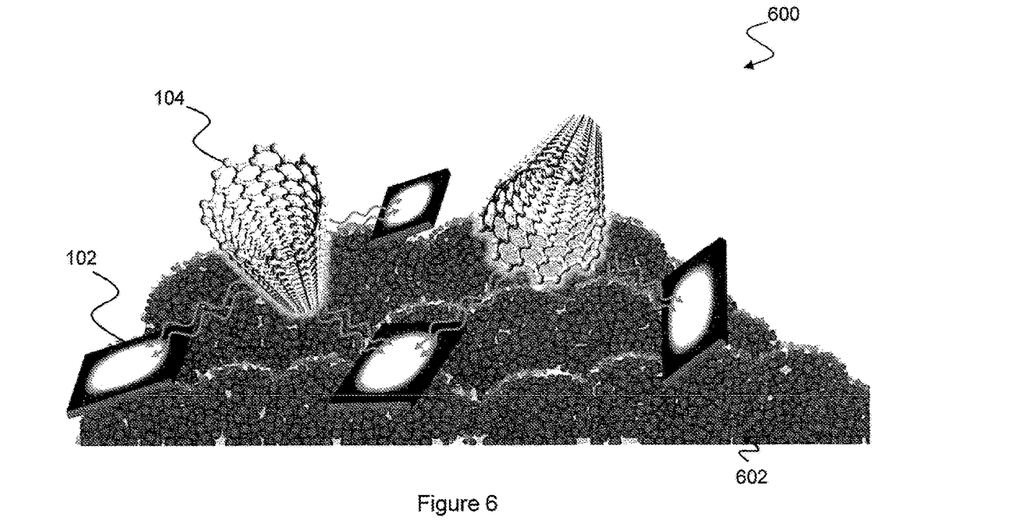
FIG. 6 is a schematic diagram illustrating an application of spaser devices embodying the invention for the treatment of cancer.

In one particular exemplary application, illustrated by the schematic diagram 600 shown in FIG. 6, spaser devices embodying the invention may be employed for the treatment of cancer.

In accordance with this aspect of the invention, a cluster of spasers comprising a plurality of GNFs 102 and CNTs 104 operates close to cancer cells 602, concentrating optical energy in large scale. This results in a strong electric field developing on the graphene resonators 102.

In particular, it is known to functionalize graphene and CNTs with targeting agents such as antibodies or receptor ligands to guide them towards cancer cells. In this way, the GNFs 102 and CNT 104 operate as a cluster of self-assembled spasers that can build up a strong electric field to destroy malignant cells. In addition to amplifying the electric field, the same CNTs 104 can also be used to deliver drugs to cancer cells, such that each CNT may be a dual vesicle for cell destruction.

Both graphene and CNTs have been tested in photothermal cancer treatment research, especially due to their optical responses in mid and near infrared regimes, in which the human body can considered to be transparent, and also due to their low in vivo toxicity. Graphene has excellent plasmonic properties, and an ability to facilitate strong light-matter interactions such that it is an advantageous choice for a spaser resonator at which plasmonic fields can be, as describe above with reference to FIGS. 1 to 5. According to an exemplary method of treatment, one of the SP modes is excited on GNFs 102 accumulated near cancer cells and receives gain from surrounding CNTs 104.

The CNTs 104 are optically pumped by an external laser source operating within the infrared regime. While the technique of external photothermal excitation of nanoparticles has been employed previously (and is therefore proven in principle), in accordance with embodiments of the invention the plasmonic field is amplified by means of stimulated emission and is therefore much stronger than a plasmonic field excited by illuminating a metal nanoparticle using an external laser. Accordingly, with optimal external energy pumping at much lower illumination power than used in current photothermal therapies, it is possible to generate highly concentrated electric fields on spaser resonators, causing selective destruction of the cancer cells.

While exemplary embodiments and variations of devices, methods and applications of the invention have been described, further modifications, alternatives and additional applications will be apparent to persons skilled in the relevant arts. The disclosed embodiments should be understood as being provided by way of example, for the purpose of teaching the features, benefits and use of the invention, but are not intended to limit the scope of the invention, as defined in the appended claims.

Appendix A

Analysis of an exemplary spaser design involves finding the SP modes supported by a square GNF, calculating the gain characteristics of the CNT, evaluating the matrix elements of the SP-exciton interaction, and analysing spaser performance.

The eigenfrequencies $\omega_l + i\gamma_l$ of the localized SP modes can be found by solving the Helmholtz equation $(\nabla^2 + k^2)E_{l,\eta} = 0$ for the electric field $E_{l,\eta}$ of the SP mode $(l,\eta)$ of wavenumber k. This is done numerically with the finite-element method using the commercial software package COMSOL Multiphysics available from COMSOL, Inc of Burlington, Mass., USA (www.comsol.com).

The GNF is assumed to have a finite thickness of $t=0.5$ nm, which is standard approach to numerical modeling of graphene. Then the three-dimensional conductivity of graphene is given by $\sigma(\omega)/t$. The quality factor $Q_l$ of the GNF resonator's mode $l$ is given by the ratio $\omega_l/(2\gamma_l)$. The plasmonic fields obtained are then quantized following the standard procedure of secondary quantization for dispersive media.

The single-wall CNT is assumed to be a rolled graphene sheet, which is characterised as follows. First, the electronic band structure of the graphene is calculated using the tight-binding model. By applying the zone folding method and the periodic boundary conditions along the chiral vector, the band energy dispersion relation for the CNT bands is derived. The summing up of the contributions from all bands gives the CNT's DOS:

$$D(E) = \frac{\sqrt{3}\, a}{\pi^2 R E_c} \sum_i^N \frac{|E|}{\sqrt{E^2 - \epsilon_i^2}}$$

In the above equation, $\alpha = 0.142$ nm is the c-c bond length, R is the CNT radius, $E_c = 3$ eV is the tight binding energy of the nanotube, $\epsilon_i = \alpha E_c |3i + 1|/2R$, and $N = 4(m^2 + mn + n2)/gcd$ (n, m) for semiconducting nanotubes. The exciton energies $E_{11}$ and $E_{22}$ can then be determined (see, e.g., graph 300 of example DOS in FIG. 3A).

The exciton wave function along the CNT of length L is assumed to be of the symmetric Gaussian form $A\exp[-(z/L)^2]$, where z is the distance from the nanotube's centre and A is the normalization constant.

The Hamiltonian of the spaser is a sum of four terms:

$$\hat{H} = \hat{H}_e + \hat{H}_{SP} + \hat{H}_{e,L} + \hat{H}_{e,SP}$$

In the above equation: $\hat{H}_e = E_{11}|1_e\rangle\langle 1_e| + E_{22}|2_e\rangle\langle 2_e|$ and $\hat{H}_{sp} = \sum_{\eta=1}^{P} E_{sp} b_{l,\eta}^{\dagger} b_{l,\eta}$ are the Hamiltonians of non-interacting excitons and SPs of mode $(l,\eta)$; $b_{l,\eta}^{\dagger}, b_{l,\eta}$ are the creation and annihilation operators of the SP mode; and $\hat{H}_{e,L}$ and $\hat{H}_{e,SP}$ are the Hamiltonians corresponding to the exciton-pump-light and exciton-SP interactions. They take the forms: $\hat{H}_{e,L} = (1/2) V_L e^{-i\omega_L t}|2_e\rangle\langle 0_e| + CC$ and $\hat{H}_{e,SP} = i\hbar g_l \sum_{\eta=1}^{P}$ $V_{l,\eta} b_{l,\eta}^\dagger |0_e\rangle\langle 1_e| + CC$, where $g_l = (\omega_l/(2\varepsilon_0)\hbar V)^{1/2}$ is the exciton-SP coupling constant, V is the normalization volume, $\omega_L$ is the excitation frequency, and CC stands for complex conjugate.

The Hamiltonian is substituted to the system of partial differential equations given in Equation 2. The solution to the system is used to find the population $\rho_{kk}$ of state $|k\rangle = |\eta+3\rangle \equiv |0_e\rangle |1_{pl}^{l,\eta}\rangle$ and the total plasmon generation rate:

$$R_l = \sum_{k=4}^{p+3} \rho_{KK} = \frac{\omega_l g_l^2 \xi_{23}}{\gamma_{22}\gamma_{33}\gamma_{pl}} \frac{\gamma_{13}}{\gamma_{13}^2 + \Delta_{13}^2} \frac{\gamma_\rho}{\gamma_\rho^2 + \Delta_\rho^2} |V_L|^2 \sum_{\eta=1}^{p} |V_{l,\eta}|^2$$

In the above equation: $\gamma_{\mu\nu}(\mu, \nu=1, 2, \ldots, p+3)$ and $\xi_{23}$ are defined in Equation 2; $\Delta_{L3} = (E_{22}/\hbar - \omega_L)$ and $\Delta_\rho = \Delta_{24} = \Delta_{25} = (E_{11} - ESP)/\hbar$; $\gamma_p = \gamma_{24} = \gamma_{25}$, and $\gamma_{pl} = \gamma_{44} = \gamma_{55}$.

The normalized plasmon generation rates $R_l$ are plotted in FIG. 5 using $\tau = 10^{-13}$ s and $\gamma_p = 10^{10}$ s$^{-1}$, while the matrix elements $V_{l,\eta}$ are numerically evaluated using the electric field distributions $E_{l,\eta}$ obtained with the finite-element method.

The claims defining the invention are as follows:

1. A spaser device comprising a graphene resonator and a carbon nanotube (CNT) gain element coupled via exciton-plasmon interaction, wherein the spaser device is configured such that, upon excitation of the CNT at a first exciton energy to cause generation of excitons in the CNT having a second exciton energy lower than the first exciton energy, a rate of generation of the excitons having the second exciton energy exceeds a gain threshold such that continuous spasing is established within the spaser device.

2. The spaser device of claim 1 wherein the graphene resonator comprises a rectangular or square graphene nanoflake (GNF).

3. The spaser device of claim 2 wherein side lengths of the GNF are between 25 nm and 100 nm.

4. The spaser device of claim 1 wherein the graphene resonator is adapted to have a selected surface plasmon (SP) mode energy by modification of an associated Fermi energy.

5. The spaser device of claim 1 wherein the CNT gain element comprises a single-walled CNT (SWNT) characterised by chirality vector (n,m) selected such that the SWNT has semiconducting properties.

6. The spaser device of claim 5 wherein the chirality of the SWNT is selected such that a band-gap energy corresponds with an SP mode energy of the graphene resonator.

7. The spaser device of claim 5 wherein the chirality vector of the SWNT is selected from the group comprising: (13,11); (12,10); (16,2); (10,9); (12,4); (14,1); (11,3); (12,1); and (11,4).

8. The spaser device of claim 7 wherein the chirality vector of the SWNT is selected from the subgroup comprising: (16,2); (12,4); (11,3); and (12,1).

9. The spaser device of claim 1 wherein a length of the CNT gain element is selected in order to maximise coupling via the exciton-plasmon interaction.

10. The spaser device of claim 9 wherein a ratio of a side length of the graphene resonator to the CNT length is within the range of 0.5 to 1.5.

11. The spaser device of claim 9 wherein the ratio of the side length of the graphene resonator to the CNT length is within the range of 1.0 to 1.3.

12. The spaser device of claim 9 wherein the ratio of the side length of the graphene resonator to the CNT length is around 1.1.

13. The spaser device of claim 1 wherein an orientation of a longitudinal axis of the CNT gain element relative to the graphene resonator is selected in order to enhance coupling between CNT excitons and resonator SPs.

14. The spaser device of claim 1 wherein a spacing between the graphene resonator and the CNT gain element is selected so as to enhance coupling between CNT excitons and resonator SPs.

15. The spaser device of claim 14 wherein the spacing is less than 10 nm.

16. The spaser device of claim 15, wherein the spacing is less than 5 nm.

17. The spaser device of claim 1 further comprising a layer of low refractive index dielectric material disposed as a spacing layer between the graphene resonator and the CNT gain element.

18. The spaser device of claim 17 wherein the spacing layer comprises SiO2 or polydimethylsiloxane (PDMS).

19. A method of establishing continuous spasing in a spaser device, comprising:
    providing a graphene resonator element and a carbon nanotube (CNT) gain element configured to form the spaser device according to any one of the preceding claims; and
    illuminating the CNT gain element using a light source having a photon energy corresponding with a first exciton energy of the CNT,
    whereby excitons having a second exciton energy less than the first exciton energy are generated in the CNT, and coupled to a surface plasmon (SP) mode of the graphene resonator, and wherein the rate of generation of excitons having the second exciton energy exceeds a gain threshold of the spaser device such that continuous spasing is established therein.

20. A method for treatment of a medical condition, such as cancer, characterised by a growth of abnormal cells, the method comprising:
    targeting the growth of abnormal cells with at least one graphene resonator element and at least one carbon nanotube (CNT) gain element to form, proximate to the growth, a spaser device according to any one of claims 1 to 18; and
    illuminating the CNT gain element using a light source having a photon energy corresponding with a first exciton energy of the CNT,
    whereby excitons having a second exciton energy less than the first exciton energy are generated in the CNT, and coupled to a surface plasmon (SP) mode of the graphene resonator, and wherein the rate of generation of excitons having the second exciton energy exceeds a gain threshold of the spaser device such that continuous spasing is established therein,
    whereby exceeding the gain threshold creates a build-up of plasmons and an electric field is generated proximate to the growth of abnormal cells sufficient to destroy the abnormal cells.

21. The method of claim 20 wherein the step of targeting the growth of abnormal cells comprises functionalizing the graphene resonator element and the CNT gain element with one or more targeting agents to guide them towards the growth of abnormal cells.

* * * * *